(12) United States Patent
Ryu et al.

(10) Patent No.: US 7,074,951 B2
(45) Date of Patent: Jul. 11, 2006

(54) PROCESS FOR MAKING DIALKYL CARBONATES

(76) Inventors: J. Yong Ryu, 10100 Bay Area Blvd., Pasadena, TX (US) 77507; Abraham P. Gelbein, 3500 Pinetree Ter., Falls Church, VA (US) 22041

( * ) Notice: Subject to any disclaimer, the term of this patent is extended or adjusted under 35 U.S.C. 154(b) by 196 days.

(21) Appl. No.: 10/821,225

(22) Filed: Apr. 8, 2004

(65) Prior Publication Data

US 2005/0203307 A1    Sep. 15, 2005

Related U.S. Application Data

(60) Provisional application No. 60/552,838, filed on Mar. 12, 2004.

(51) Int. Cl.
*C07C 67/18* (2006.01)
(52) U.S. Cl. ...................... 558/277; 558/262
(58) Field of Classification Search ............. 558/277, 558/262
See application file for complete search history.

(56) References Cited

U.S. PATENT DOCUMENTS

| | | | | |
|---|---|---|---|---|
| 5,788,915 | A | * | 8/1998 | Blount ..................... 252/609 |
| 6,031,122 | A | * | 2/2000 | Mizukami et al. ......... 558/277 |
| RE37,337 | E | | 8/2001 | Ryu .......................... 558/277 |
| 6,359,163 | B1 | | 3/2002 | Mizukami et al. ......... 558/277 |
| 6,392,078 | B1 | * | 5/2002 | Ryu et al. ................. 558/277 |

FOREIGN PATENT DOCUMENTS

| | | | |
|---|---|---|---|
| EP | 1 167 339 A2 | | 1/2002 |
| WO | WO 95/17369 | * | 6/1995 |
| WO | WO 95/17369 A1 | | 6/1995 |
| ZA | 6804613 A | * | 12/1968 |

OTHER PUBLICATIONS

Peter Ball, Heinz Fullmann, Reinhold Schwalm and Walter-Heitz, Synthesis of Carbonates and Polycarbonates by Reaction of Urea with Hydroxy Compounds, C1 Mol. Chem., 1984, vol. 1, pp. 95-108.

* cited by examiner

*Primary Examiner*—Kamal A. Saeed
*Assistant Examiner*—Yong Chu
(74) *Attorney, Agent, or Firm*—Kenneth H. Johnson

(57) ABSTRACT

A process for the production of dialkyl carbonates from the reaction of alcohol, for example $C_1$–$C_3$ alcohols, with urea is disclosed wherein the water and ammonium carbamates impurities in the feed are removed in a prereactor. The water is reacted with urea in the feed to produce ammonium carbamate which is decomposed along with the ammonium carbamates originally in the feed to ammonia and carbon dioxide. In addition some of the urea is reacted with the alcohol in the first reactor to produce alkyl carbamate which is a precursor to dialkyl carbonate. Dialkyl carbonates are produced in the second reaction zone. The undesired by-product N-alkyl alkyl carbamates are continuously distilled off from the second reaction zone along with ammonia, alcohol and dialkyl carbonates under the steady state reactor operation. N-alkyl alkyl carbamates can be converted to heterocyclic compounds in a third reaction zone to remove as solids from the system.

6 Claims, 5 Drawing Sheets

PROCESS FOR MAKING DIALKYL CARBONATES

This application claims the benefit of provisional application 60/552,838 filed Mar. 12, 2004.

BACKGROUND OF THE INVENTION

1. Field of the Invention

The present invention relates to a process for the production of dialkyl carbonates, particularly $C_1$–$C_3$ dialkyl carbonates wherein the reaction occurs simultaneously with separation of the reactants and the carbonate products. More particularly the invention relates to a process wherein alcohol is reacted with urea and/or alkyl carbamate in the presence of a complex compound catalyst. More particularly the invention relates to a process wherein feed stream impurities are removed to produce stable catalyst performance, improved reaction rates and trouble free downstream operation of equipment.

2. Related Art

Dialkyl carbonates are important commercial compounds, the most important of which is dimethyl carbonate (DMC). Dimethyl carbonate is used as a methylating and carbonylating agent and as a raw material for making polycarbonates. It can also be used as a solvent to replace halogenated solvents such as chlorobenzene. Although the current price of both dimethyl carbonate and diethyl carbonate is prohibitively expensive to use as fuel additive, both could be used as an oxygenate in reformulated gasoline and an octane component. Dimethyl carbonate has a much higher oxygen content (53%) than MTBE (methyl tertiary butyl ether) or TAME (tertiary amyl methyl ether), and hence not nearly as much is needed to have the same effect. It has a RON of 130 and is less volatile than either MTBE or TAME. It has a pleasant odor and, unlike ethers, is more readily biodegradable.

In older commercial processes dimethyl carbonate was produced from methanol and phosgene. Because of the extreme toxicity and cost of phosgene, there have been efforts to develop better, non-phosgene based processes.

In one new commercial process, dimethyl carbonate is produced from methanol, carbon monoxide, molecular oxygen and cuprous chloride via oxidative carbonylation in a two-step slurry process. Such a process is disclosed in EP 0 460 735 A2. The major shortcomings of the process are the low production rate, high cost for the separation of products and reactants, formation of by-products, high recycle requirements and the need for corrosion resistant reactors and process lines.

Another new process is disclosed in EP 0 742 198 A2 and EP 0 505 374 B1 wherein dimethyl carbonate is produced through formation of methyl nitrite instead of the cupric methoxychloride noted above. The by-products are nitrogen oxides, carbon dioxide, methylformate, etc. Dimethyl carbonate in the product stream from the reactor is separated by solvent extractive distillation using dimethyl oxalate as the solvent to break the azeotropic mixture. Although the chemistry looks simple and the production rate is improved, the process is very complicated because of the separation of a number of the materials, balancing materials in various flow sections of the process, complicated process control and dealing with methyl nitrite, a hazardous chemical.

In another commercial process dimethyl carbonate is produced from methanol and carbon dioxide in a two-step process. In the first step cyclic carbonates are produced by reacting epoxides with carbon dioxide as disclosed in U.S. Pat. Nos. 4,786,741; 4,851,555 and 4,400,559. In the second step dimethyl carbonate is produced along with glycol by exchange reaction of cyclic carbonates with methanol. See for example Y. Okada, et al "Dimethyl Carbonate Production for Fuel Additives", ACS, *Div. Fuel Chem., Preprint*, 41(3), 868, 1996, and John F. Knifton, et al, "Ethylene Glycol-Dimethyl Carbonate Cogeneration", *Journal of Molecular Chemistry*, vol. 67, pp 389–399, 1991. While the process has its advantages, the reaction rate of epoxides with carbon dioxide is slow and requires high pressure. In addition, the exchange reaction of the cyclic carbonate with methanol is limited by equilibrium and methanol and dimethyl carbonate form an azeotrope making separation difficult.

It has been known that dialkyl carbonates can be prepared by reacting primary aliphatic alcohols such as methanol with urea (1) in the presence of various heterogeneous and homogeneous catalysts such as dibutyltin dimethoxide, tetraphenyltin, etc. See for example P. Ball et al, "Synthesis of Carbonates and Polycarbonates by Reaction of Urea with Hydroxy Compounds", C1 *Mol. Chem.*, vol. 1, pp 95–108, 1984. Ammonia is a coproduct and it may be recycled to urea (2) as in the following reaction sequence.

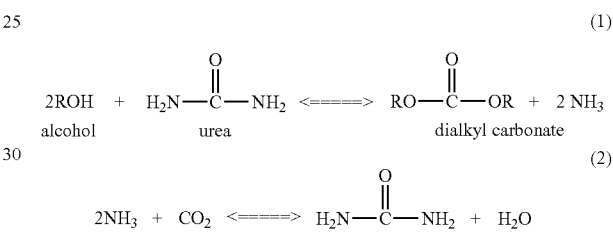

Carbamates are produced at a lower temperature followed by production of dialkyl carbonates at higher temperature with ammonia being produced in both steps.

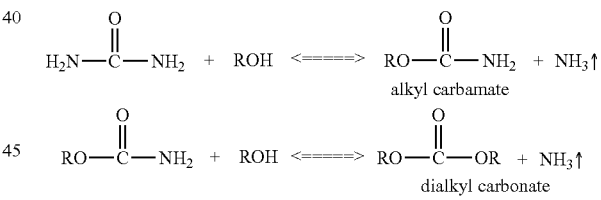

As noted the above two reactions are reversible under reaction conditions. The order of catalytic activity of organotin compounds is $R_4Sn < R_3SnX << R_2SnX_2$, wherein $X=Cl$, RO, RCOO, RCOS. A maximum reaction rate and minimum formation of by-products are reported for dialkyl tin (IV) compounds. For most catalysts (Lewis acids), higher catalyst activity is claimed if the reaction is carried out in the presence of an appropriate cocatalyst (Lewis base). For example, the preferred cocatalyst for organic tin (IV) catalysts such as dibutyltin dimethoxide, dibutyltin oxide, etc. are triphenylphosphine and 4-dimethylaminopyridine. However, thermal decomposition of intermediate alkyl carbamates and urea to isocyanic acid (HNCO) or isocyanuric acid ((HNCO)$_3$) and alcohol or ammonia (a coproduct of urea decomposition) is also facilitated by the organotin compounds such as dibutyltin dimethoxide or dibutyltin oxide employed in the synthesis of dialkyl carbamates. WO 95/17369 discloses a process for producing dialkyl carbonate such as dimethyl carbonate in two steps from alcohols and urea, utilizing the chemistry and catalysts published by P. Ball et al. In the first step, alcohol is reacted with urea to produce an alkyl carbamate. In the second step, dialkyl carbonate is produced by reacting further the alkyl carbamate with alcohol at temperatures higher than the first step. The reactions are carried out by employing an autoclave reactor. However, when methanol is reacted with methyl carbamate or urea, N-alkyl by-products such as N-methyl methyl carbamate (N-MMC) and N-alkyl urea are also produced according to the following reactions:

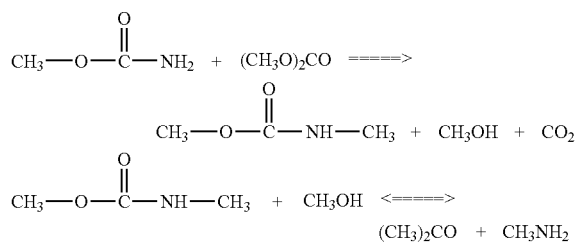

The dialkyl carbonate is present in the reactor in an amount between 1 and 3 weight % based on total carbamate and alcohol content of the reactor solution to minimize the formation of the by-products.

In U.S. Pat. No. 6,010,976, dimethyl carbonate (DMC) is synthesized from urea and methanol in high yield in a single step in the presence of high boiling ethers and a novel homogeneous tin complex catalyst.

The ether solvent also serves as complexing agent to form the homogenous complex catalyst from dibutyltin dimethoxide or oxide in situ.

The separation of materials involved in the DMC processes is very important for the commercial production of DMC for economic reasons. EP 0 742 198 AI and U.S. Pat. No. 5,214,185 disclose the separation of DMC from a vapor mixture of methanol and DMC by using dimethyl oxalate (DMOX) as extraction solvent. Because of the high melting point of DMOX (54° C.), using DMOX is inconvenient and adds an extra cost to the separation.

Both urea and alcohols are highly hygroscopic. Urea contains an ammonium carbamate impurity. Therefore, water and ammonium carbamate are impurities in urea and alcohol feed. It has been found that impurities such as water, ammonium carbamate, etc, in the urea and alcohol feeds cause catalyst deactivation and line plugging on cold spots in the cooling section (the condenser) for the overhead vapor stream from the reactor. Water causes the deactivation of catalyst containing alkyoxy groups, for example, the methoxy groups on the organotin complex compound molecules are highly reactive with water molecules resulting in hydrolysis of the bond between the tin atom and oxygen atom of methoxy group. Ammonium carbamate causes problems for controlling the backpressure in the dialkyl carbonate producing reactor and plugging the cooling system (condenser) of the product vapor stream from the dialkyl reactor, because of the deposition of ammonium carbamate.

SUMMARY OF THE INVENTION

Briefly the present invention is an improved process for production of dialkyl carbonate comprising the steps of:

(a) feeding a stream containing urea, alcohol, water and ammonium carbamate to a first reaction zone:
(b) concurrently in said first reaction zone,
(i) reacting water with urea to form ammonium carbamate,
(ii) decomposing the ammonium carbamate in the feed and the ammonium carbamate from the reaction of water with urea into ammonia and carbon dioxide, and
(c) removing ammonia, carbon dioxide and said alcohol from said first reaction zone as a first overheads;
(d) removing urea and said alcohol from said first reaction zone;
(e) feeding said urea and said alcohol to a second reaction zone;
(f) reacting said alcohol and urea in the presence of a homogeneous catalyst comprising an organotin complex compound of dialkylmethoxide in a high boiling solvent to form dialkyl carbonate and
(g) removing dialkyl carbonate and said alcohol from said second reaction zone.

Dialkyl carbonates are prepared by reacting alcohols, preferably $C_1$–$C_3$ alcohols, with urea or alkyl carbamate or both in the presence of a complex of organotin compound with a high boiling electron donor compound acting as a solvent, preferably dibutyltin dialkoxide complex compound and high boiling oxygen containing organic solvent, wherein the reaction is preferably carried out in the reboiler of a distillation still or a stirred tank reactor with concurrent distillation of the dialkyl carbonate. The urea and alcohol feeds are purified by removing water and ammonium carbamates, N-alkylated by-product and a minor fraction of alkylcarbamate.

The water is removed by reacting it with urea in a prereactor having a preliminary reaction zone. Ammonium carbamate is removed by decomposition to ammonia and carbon dioxide in the prereactor. In addition urea is partially and selectively converted to alkyl carbamate in the prereactor which results in a faster reaction rate in the primary reactor, a reduction of alcohol recycle to the primary reactor from the dialkyl carbonate recovery unit or column and a higher concentration of dialkyl carbonate in the overhead stream from the primary reactor. A higher concentration of dialkyl carbonate in the overhead stream from the primary reactor reduces the cost of separation of the dialkyl carbonate.

Figure 1:
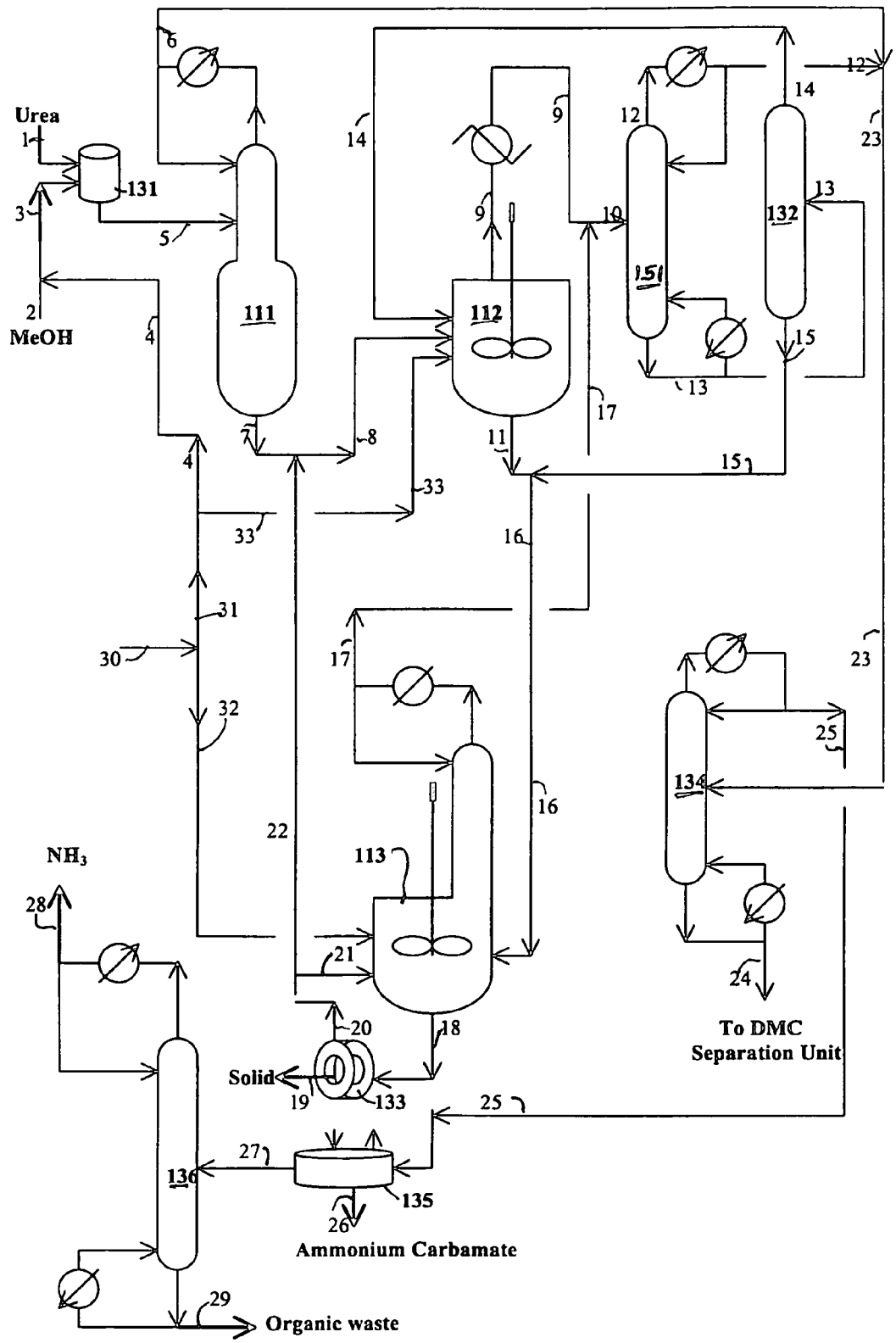
FIG. 1 is a simplified flow diagram of one embodiment for producing DMC according to the present invention.

FIG. is 5 a simplified flow diagram of a catalytic stirred tank reactor with an attached distillation column embodiment for the present process.

DETAILED DESCRIPTION OF THE PREFERRED EMBODIMENT

The water impurity in the urea and alcohol feeds is removed by reacting the water with urea in a prereactor while ammonium carbamate is removed by decomposing it to ammonia and carbon dioxide in the prereactor. The prereactor must be operated under favorable conditions for the decomposition such that the ammonia and carbon dioxide may be removed as vapors. If the decomposition is incomplete the unconverted ammonium carbamate will enter the primary reactor and be converted to urea and water as it decomposes to ammonia and carbon dioxide causing the deactivation of the catalyst. Urea is partially converted to alkyl carbamate in the prereactor. The following necessary reactions occur in the prereactor:

  (1)

  (2)

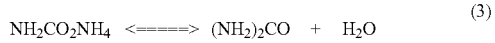  (3)

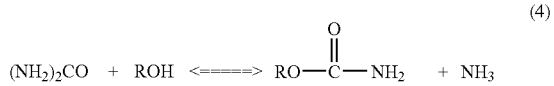  (4)

Since the above four are equilibrium reactions and must occur simultaneously in the preliminary reaction zone in the prereactor, controlling the temperature and pressures of the prereactor and the primary reactor is important. The reactions (1), (2), (3) and (4) are carried out in the prereactor at a temperature from 200 to 380° F., preferably from 250 to 350° F. in liquid phase in the prereactor. The preferred range of the overhead pressure of the prereactor is from about 30 to 300 psig. However, the overhead pressure is determined mainly by the desired temperature of the prereactor column and the composition of the liquid in the reactor. Reaction (4) proceeds to equilibrium in the absence of a catalyst, but the reaction is faster in the presence of a catalyst such as dibutyltin dialkoxide complex catalyst and weakly acidic or basic heterogeneous catalyst such as zinc oxide, tin oxide, titanium oxide, zirconium oxide, molybdenum oxide, talcite, calcium carbonate, zinc carbonate hydroxide, zirconium carbonate hydroxide, etc. supported on a inert support such as silica, high temperature (>850° C.) calcined alumina. The preferred concentration of urea in the liquid phase in the preliminary reaction zone under given conditions is less than about 80 wt. %, preferably 50 wt. %. The partial pressures of ammonia and carbon dioxide must be kept below the decomposition pressure of ammonium carbamate to allow the decomposition of ammonium carbamate. It is also highly desirable to effectively remove the products, ammonia and carbon dioxide, from the preliminary reaction zone of the prereactor, preferably as a vapor mixture along with alcohol and any inert stripping gas employed as an option. Alcohol vapor may be used as the sole stripping gas if desired. Thus, the improvement is in a process for the production of dialkyl carbonates by the reaction of reactants comprising urea and alcohol having water and ammonium carbamate as impurities comprising the steps of:

(a) feeding reactants comprising urea and alcohol to a primary reaction zone;

(b) feeding an organotin compound and a high boiling electron donor atom containing solvent to said primary reaction zone; and (c) concurrently in said primary reaction zone
   (i) reacting alcohol and urea in the presence of said organotin compound and said high boiling electron donor atom containing solvent to produce dialkyl carbonate; and (ii) removing the dialkyl carbonate and ammonia from said primary reaction zone as vapor, wherein the improvement is the use of a preliminary reaction zone before the primary reaction zone to remove water, and ammonium carbamate from said reactants, by feeding the reactants, first to the preliminary reaction zone under conditions to react said water with urea to form ammonium carbamate and decompose ammonium carbamate to ammonia and carbon dioxide and removing the ammonia and carbon dioxide from said reactants prior to feeding the reactants in step (b), preferably at a temperature in the range from 200 to 380° F., more preferably from 250 to 350° F. and preferably in liquid phase. Preferably a portion of the urea and alcohol react to form alky carbamate in the preliminary reaction zone.

A preferred embodiment of the process for the production of dialkyl carbonates comprises the steps of:

(a) feeding urea, $C_1$–$C_3$ alcohol prereaction zone;
   (i) cleaning the impurities in feeds in the prereactor;
   (ii) removing ammonia, carbon dioxide and alcohol as vapor stream;
   (iii) reacting a portion of urea and alcohol to alkyl carbamate; and
   (iv) removing a liquid stream containing alkyl carbamate, urea and alcohol to introduce to a primary reaction zone;

(b) feeding an organotin compound and a high boiling electron donor atom containing solvent to said primary reaction zone;

(c) concurrently in said primary reaction zone
   (i) reacting $C_1$–$C_3$ alcohol, urea and alkyl carbamate in the presence of said organotin compound and said high boiling electron donor atom containing solvent to produce dialkyl carbonate; and
   (ii) removing the dialkyl carbonate and ammonia, ether, carbon dioxide, N-alkyl alkyl carbamate and alkyl carbamate from said primary reaction zone as vapor; and (d) converting N-alkyl alkyl carbamate separated from the vapor stream from primary reactor and in a small slipstream of liquid reaction medium from primary reaction zone to said heterocyclic compounds ($(RNCO)_3$, where R is H or $C_nH_{2n+1}$ and n=1, 2 or 3) in said third clean-up reaction zone and converting alkyl carbamate to dialkyl carbonate;
   (i) removing heterocyclic compounds in the stream from the third reaction zone as solids;
   (ii) returning the reaming liquid stream to the primary reaction zone and the clean-up reaction zone, and
   (iii) removing ammonia, alcohol and dialkyl carbonate as overhead vapor stream This embodiment provides improvements which include the use of a preliminary reaction zone to remove water, and ammonium carbamate from said urea and alcohol, preferably at a temperature in the range from 200 to 380° F., more preferably from 250 to 350° F. and preferably in liquid phase and the use of a clean-up reaction zone to convert the by-product N-alkyl alkyl carbamate to heterocyclic compounds at a temperature in the range from 300 to 400° F. in liquid phase to remove as solid from the system.

The preferred prereactor is double diameter tower reactor (wider diameter at lower section). The urea feed solution in alcohol is introduced to the column prereactor at the middle section of narrower diameter upper section. The ammonium carbamate in the urea feed is decomposed to ammonia and carbon dioxide. The temperature of the column is maintained at a temperature from about 200 to about 380° F. under from 50 to 350 psig. The light reaction products, ammonia and carbon dioxide, are removed from the column as an overhead vapor stream along with alcohol vapor. Urea in the feed stream is, at least, partially converted to alkyl carbamate in this prereactor. This reaction is exothermic. The conversion of urea is higher than 10%, preferably higher than 50%. The conversion of urea to alkyl carbamate can be carried out in the absence of the complex catalyst. But with the catalyst the conversion rate is faster.

Removing water and ammonium carbamate impurities in the feed streams solves the problems associated with keeping the catalyst in the active state, controlling overhead pressure of the distillation column, and plugging of cooling area of overhead vapor stream from primary reactor by deposition of ammonium carbamate. Cleaning-up of the impurities in feeds is carried out in a prereactor, which is a double diameter distillation column reactor. Removing the impurities in the feed streams is the primary objective of the prereactor. Further improvement is made by at least partially converting urea to alkyl carbamate in the prereactor, which results in faster reaction rate of producing dialkyl carbonate in the primary reactor, a reduction of alcohol recycle to the primary reactor from dialkyl carbonate recovery unit because of higher concentration of dialkyl carbonate in the overhead stream from the primary reactor. In making dialkyl carbonate, a higher concentration of dialkyl carbonate in the overhead stream from the primary reactor reduces the separation cost of dialkyl carbonate.

The primary reactor, where dialkyl carbonate is formed, is stirred tank reactor equipped with a heat exchanger to recover the latent heat of the product vapor stream from the primary reactor. The recovered heat is used to recycle alcohol from alcohol recovery column to primary reactor. It is not necessary, but optional that the liquid reaction medium is mechanically stirred. In the present invention, the reaction/distillation column of the primary reactor is operated unconventionally so that the undesired N-alkylated by-products are removed from the liquid reaction zone as parts of overhead product stream, which allows maintaining the by-products at the minimal level so that the reactor can be operated at a constant liquid level without filling the liquid reaction zone with undesired by-products for an extended period of reactor operation without any interruption. This is highly desirable for the successful commercial production of dialkyl carbonate. Lower concentrations of urea, alkyl carbamate and dialkyl carbonate in the liquid medium are utilized to minimize the rate of the formation of N-alkylated by-products, which is accomplished by using a higher concentration of high boiling solvent such as triglyme. However, if the alkyl carbamate concentration is too low an unacceptably low space yield of DMC can occur.

To avoid accumulation of the by-products such as N-alkyl alkyl carbamate and heterocyclic compounds in the primary reactor, it was discovered that the N-alkyl alkyl carbamate could continuously be distilled off from the liquid reaction medium, while concurrently performing the dialkyl carbonate producing reaction, by controlling both temperature and pressure of the distillation column of the primary reactor vapor stream, and be converted to heterocyclic compounds, which can be removed as solids from the system. In other words, it was discovered that steady concentrations of N-alkyl alkyl carbamate and heterocyclic compounds in a given liquid reaction volume of the primary reaction zone could be maintained under a steady station reactor operation condition. It was also discovered that maintaining the skin temperature of any internal portion of the primary reactor at a temperature below about 550° F., preferably below 450° F. is highly desirable to minimize the formation of heterocyclic compounds in the primary reaction zone. The conversion of N-alkyl alkyl carbamate to heterocyclic compounds is carried out by employing a third clean-up reaction zone.

The preferred clean-up reactor for this purpose is a stirred tank reactor equipped with an attached distillation column, a condenser and reflux drum. The by-product N-alkyl alkyl carbamate produced by alkylation of alkyl carbamate with dialkyl carbonate in the primary reaction zone is continuously removed as a part of overhead vapor stream along with other products by operating the vapor temperature from the primary reaction zone at a column temperature higher than about 255° F., preferably higher than 265° F.

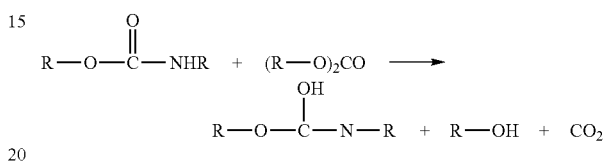

The N-alkyl alkyl carbamate is separated from the overhead stream from the primary reactor and introduced to the clean-up reactor. The clean-up reactor is preferably operated at a temperature of the liquid reaction medium in range from 330 to 400° F. It is important that the column temperature and the column overhead pressure are controlled so that the overhead vapor stream does not contain N-alkyl alkyl carbamate. In general, the clean-up reactor is operated at a reaction temperature and an overhead pressure at, at least, 2° F. and 5 psig higher than those of the primary reactor.

The technique of removing the by-products disclosed in this invention can be extended to the prior art such as U.S. Pat. No. 6,359,163 B2 (2002) and WO 95/17369 (1995), U.S. Pat. No. 6,031,122 (2000), and EP 1167339 (2002) producing dialkyl carbonate from urea and an alcohol regardless whether a solvent is used or not in the primary reactor and the clean-up reactor.

For the production of heavier alkyl carbonate such as dipropyl carbonate, dibutyl carbonate, etc., removing N-alkyl alkyl carbamate from the primary reactor as parts of the overhead stream becomes difficult. Therefore, a liquid slip stream is taken out of the primary reactor in larger quantity to the clean-up reactor. N-alkyl alkyl carbamate in this slip stream is converted to separable high boiling point materials in the clean-up reactor as disclosed in this invention. After removing high boiling waste materials in the bottom stream from the clean-up reactor, the remaining liquid stream may be returned to the primary reactor and the clean-up reactor.

Various physical devices may be utilized as the prereactor. These include a distillation column reactor, a stirred tank reactor, bubble reactor, tubular reactor, boiling point reactor or any combination thereof. The preferred device is a distillation column reactor, in which the reactions are carried out under reaction/distillation conditions. Despite the equilibrium nature of the reactions (1), (2) and (3), employing the distillation column reactor allows driving the three reactions to the right, that is, complete removal of water and ammonium carbamate in the feed streams. Urea is partially converted to alkyl carbamate in the prereactor according to equilibrium reaction (4). By removing ammonia from the reaction zone as an overhead gas mixture, the reaction (4) can be forced to the right side of the reaction as well. The partial conversion of urea to alkyl carbamate increases the rate of conversion of alkyl carbamate to dialkyl carbonate in the primary reactor and results in a higher concentration of dialkyl carbonate in the overhead stream from the primary reactor because the reaction of urea with alcohol to produce dialkyl carbonate occurs in two steps and reaction (4) is the first step.

The dialkyl carbonate forming reaction is as follows:

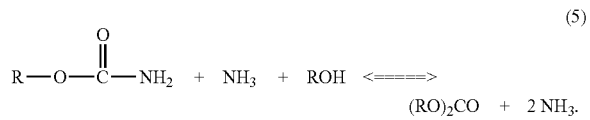

(5)

Reaction (5) is carried out in the primary reactor in the presence of a high boiling solvent in the reaction/distillation mode to create a favorable condition for fast removal of dialkyl carbonate from the reaction medium as soon as it is produced. The rate of forming dialkyl carbonate in the primary reactor is more sensitive to the concentration of ammonia in reaction medium in the primary reactor than the rate of forming alkyl carbamate in the prereactor due to the chemical thermodynamics. The rate of forming dialkyl carbonate becomes faster, if, at a given concentration of alkyl carbamate, there is a lower ammonia concentration in the liquid reaction medium in the primary reactor. The temperature of the reaction medium in the primary reactor is from about 300 to about 450° F., preferably from about 320 to 400° F., most preferably from about 330 to 360° F. under a pressure from about ambient to 150 psig, preferably from 30 to 120 psig. Any combination of desired temperature and pressure, which results in high selectivity of dialkyl carbonate, can be obtainable by choosing a proper high boiling solvent and controlling the concentration of the solvent in the primary reactor. It is highly desirable that the primary reactor be operated to have the temperature of the overhead vapor at least about 300° F., preferably higher than about 320° F. for the recovery of the latent heat of the overhead vapor stream to be used for the alcohol recycle as super heated alcohol vapor to the primary reactor and prereactor.

Using high boiling solvent in the primary reactor allows carrying out the reaction under low pressure and low concentration of carbamate in the liquid reaction medium. Lower pressure favors faster removal of dialkyl carbonate from the liquid reaction medium to the vapor phase, resulting in lower concentrations of dialkyl carbonate in the liquid reaction medium. The lower the concentrations of dialkyl carbonate and carbamate/urea in the liquid reaction medium, the lower the undesired by-products associated to N-alkylation and the decomposition products of urea, alkyl carbamate and N-alkylated products in the primary reactor. The preferred solvent for the synthesis of dialkyl carbonates should have the following properties: (1) The solvent should boil at least, 20° F. higher temperature than the boiling point of the dialkyl carbonate product; and (2) It should not form an azeotropic mixture with dialkyl carbonate. The examples of such a solvent are high boiling ethers, ketones, hydrocarbons, and esters or mixtures of these; triethylene glycol dimethyl ether, tetraethylene glycol dialkyl ether, anisol, dimethoxy benzene, dimethoxy toluene, alkyl oxalate, decaline, tetraline, xylene, decane, etc. or mixtures of these.

A super heated alcohol vapor stream is directly introduced into the liquid reaction zone to supply the heat of reaction for the conversion of alkyl carbamate to dialkyl carbonate which is a slightly endothermic reaction, and strip off dialkyl carbonate and ammonia from the liquid reaction medium as soon as dialkyl carbonate is produced. The desired total concentration of alkyl carbamate and urea combined in the reaction medium is from about 10 to about 60 wt. %, preferably from about 15 to about 50 wt. % of the total materials in the liquid reaction medium. The desired concentration of dialkyl carbonate in the reaction medium is from about 0.5 to about 12 wt. %, preferably from about 2 to about 9 wt. % based on the total content of the liquid reaction medium. The mole ratio of alkyl carbamate to alcohol in the liquid reaction medium is from 0.2:1 to 2:1, preferably from 0.3:1 to 1.5:1. The concentration of organotin complex catalyst is from about 2 to about 20 wt. % tin, preferably from 5 to about 17 wt. % tin based on the total content of all the materials in the liquid reaction zone in the primary reactor. Note that the catalyst also catalyzes the undesired side-reactions discussed above. Carrying out the reaction at lower temperature reduces the side-reactions. However, the rate of producing dialkyl carbonate is also lower, which may not be acceptable for the commercial production of DMC. The desired concentration of high boiling solvent in the reaction medium in the primary reactor is from about 2 to about 65 wt. %, preferably from 2.5 to 55 wt. % of the total material in the reaction medium.

The working catalyst under steady state reaction conditions is an organotin complex catalyst system derived from the organotin complex compound of dialkyltin dialkoxide, $R'_{4-n}Sn(OR)_n \cdot xL$ (Where R' is alkyl group, aryl or aralkyl group; R=alkyl; n=1 or 2; x=1 or 2; L is electron donor atom containing monodentate or bidentate liqand). The examples of L are electron donor ligand molecules such as ethers, esters, ketones, aldehydes, organic phosphines or mixtures of these; triethylene glycol dimethyl ether, tetraethylene glycol dimethyl ether, dimethyl oxalate, dimethyl malonate, dimethyl succinate, anisol, dimethoxy benzene, dimethoxy toluene, ethylene glycol, catecol, 1,4-dioxane-2,3-diol, 2-methyltetrahydrfuran-3-one, 2,3-pentanedione, 2,4-pentanedione, 3-methyltetrahydropyran, triphenylphosphine, etc. The homogeneous catalyst system is a quasi-equilibrium mixture of various organotin species. Suitable catalysts of this type and their method of manufacture are described in U.S. Pat. Nos. 6,010,976 and 6,392,078 which are incorporated herein in their entirety.

The working catalyst system under the steady state reaction condition is a mixture of various soluble organotin monomer, dimer and oligomer species, which are produced by a number of possible reactions. These various organotin catalyst species are more or less in quasi-equilibrium state under a given reaction condition. Dialkyltin oxide, dialkyltin halides, dialkyltin bis(acetylacetonate) and dialkyltin carboxylates such as dibutyltin diacetate, dialkyltin oxalate, dibutyltin malonate, dibutyltin diacetate, dibutyltin bis (acetylacetonate) etc. can be used to form the soluble tin complex catalyst species in situ at the start-up of the primary reactor by reacting with alcohol in the presence of a high boiling solvent such as triglyme. The alkyl groups attached to tin atoms can be the same or different. For example, the catalyst precursor can be dibutyltin, butylbenzyltin, butylphenyltin, butyloctyltin or di-2-phenylethyltin dialkoxide, dihalides, hydroxyhalide, diacetate or oxide. Water, carboxylic acid or hydrochloric acid co-products are continuously removed from the liquid reaction medium as an overhead vapor stream in the presence of high boiling solvent under low pressure. The suitable temperature for the catalyst forming reaction is from about 200 to about 400° F. and pressure from about ambient to 150 psig. In a preferred embodiment, methanol, ethanol or propanol depending on the intended dialkyl carbonate product is continuously pumped into the primary reactor. Either methanol or ethanol is acceptable for the production of MEC. The catalyst forming reaction is advantageously carried out in the presence of dilute alkyl carbamate, N-alkyl alkyl carbamate or dialkyl solution in the primary reactor. It is understood that during this catalyst forming reaction the operation of the distillation column should be operated under conditions, which allow removing co-products water, carboxylic acid or hydrogen chloride as an overhead stream along with alcohol as an overhead product from the reaction zone. For the dimethyl carbonate production, the soluble organotin complex catalyst system is formed by simply mixing dibutyltin dimethoxide with triglyme (as a complex agent for the formation of organotin complex catalyst) and methanol in the primary reactor prior to initiating the dialkyl carbonate forming reaction in the presence of a high boiling solvent. For diethyl carbonate production, the soluble organotin complex catalyst system is preferably formed by using dibutyltin dimethoxide with triglyme and ethanol in a primary reactor. As the reaction proceeds, the methoxy groups on the catalyst are replaced with ethoxy groups.

Figure 2:
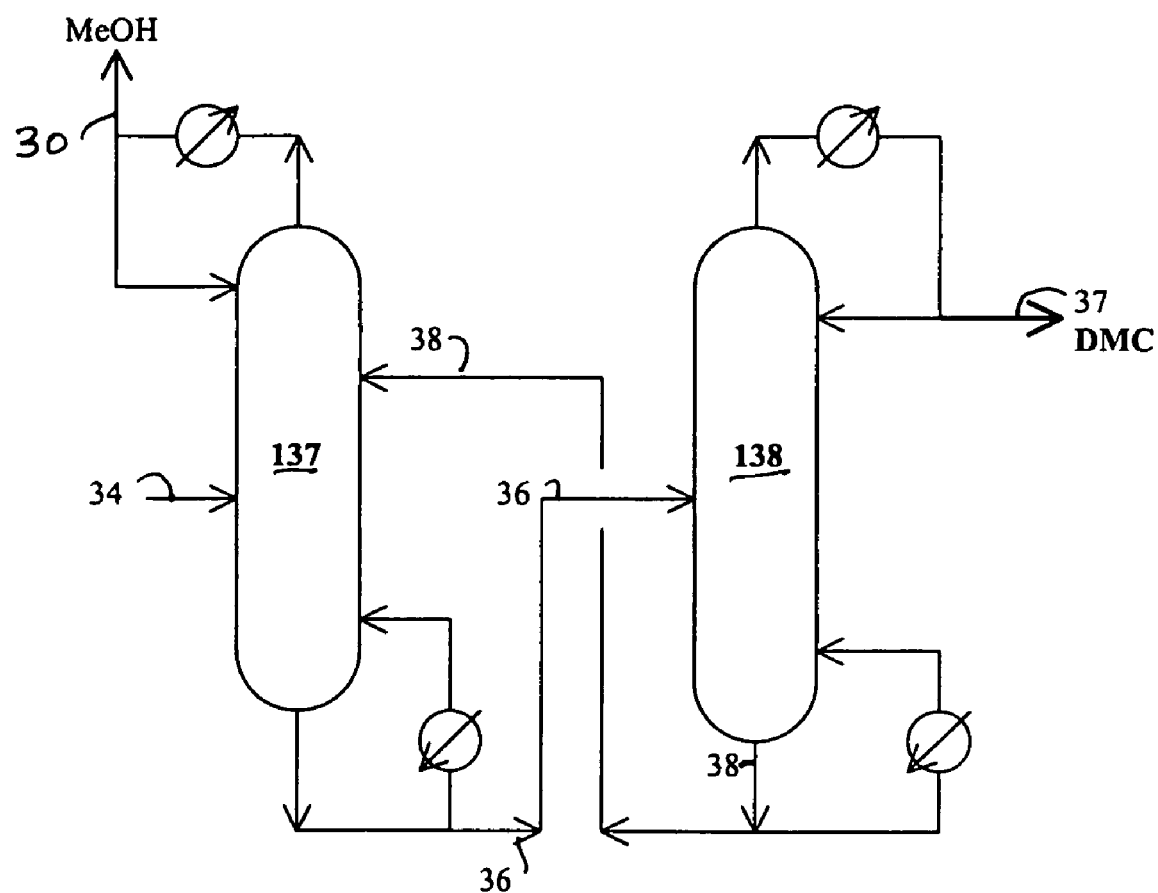
FIG. 2 is a simplified flow diagram of a DMC separation unit.

Referring now to FIG. 1 there is shown a simplified flow diagram of one embodiment of the invention. FIG. 1 illustrates the flow diagram of the improved process excluding the DMC separation unit. The DMC separation unit is illustrated in FIG. 2. A reaction/distillation column reactor 111 is used as the prereactor to remove the impurities in the feed streams and for the partial conversion of urea to methyl carbamate. Urea solution is prepared in the drum 131 by mixing urea feed 1 and methanol stream 3. The methanol stream is comprised of the fresh methanol feed stream 2 and a methanol recycle stream 4, which is a portion of the methanol recycle stream 30 from the DMC separation unit. The methanol recycle stream 30 from the DMC separation unit (shown in FIG. 2) splits into three streams (4 and 33 via 31, and 32) to be used for the preparation of urea solution, the primary reactor 112 and the clean-up reactor 113. The urea solution feed 5 from the drum 131 is introduced to the middle of upper narrower column section of the double diameter tower reactor 111. The reactor 111 serves as a prereactor to clean up the impurities (water and ammonium carbamate) in the methanol and urea feeds, and to partially covert urea to MC. A vapor stream 6 from the prereactor 111 is composed of ammonia, carbon dioxide and methanol. The cleaned mixed solution of MC and urea in methanol is removed from the prereactor 111 as bottom stream 7 and combined with the recycle liquid stream 22 from the cooling/filter system 133 via the line 20 to the stream 8. Liquid recycle stream 20 from the cooling/filter system 133 splits into two streams (21 and 22) to recycle to primary reactor 112 and clean-up reactor 113. The combined stream 8 is introduced to the primary reactor (stirred tank reactor or optionally bubble column reactor) 112. The recycle methanol stream 33 from the DMC separation unit is introduced into the primary reactor 112 as super heated methanol vapor. The overhead recycle stream 14 from the flash column 132 is introduced to the primary reactor. The stream 14 is comprised of mostly MC and minor amounts of N-MMC and methanol. The overhead vapor stream 9 from the primary reactor 112 is comprised of ammonia, $CO_2$, dimethyl ether, methanol, DMC, MC, N-MMC, TG and a small amount of organotin catalyst. This overhead stream 9 from the primary reactor 112 is combined with the overhead stream 17 from the clean-up stirred tank reactor 113 to the stream 10. The stream 17 is comprised of ammonia, $CO_2$, dimethyl ether, methanol and DMC. The combined stream 10 is introduced to the distillation column 151 to separate the components, ammonia, $CO_2$, dimethyl ether, methanol and DMC from the rest of heavier components in the stream. Overhead stream 12 from the column 151 is combined with the overhead stream 6 from the prereactor reactor 111 to the stream 23. The combined stream 23 is introduced to the distillation column 134. Overhead stream 25 from the column 134 is sent to the ammonium carbamate removing system 135, where the stream 25 is suitably cooled to cause the reaction of $CO_2$ and ammonia to ammonium carbamate and precipitation of solid ammonium carbamate. Solid ammonium carbamate may be removed by using a filter or hydroclone. Stream 27 from the ammonium carbamate removing system 135 is introduced to the distillation column 136 to recover ammonia. Overhead stream 28 from the column 136 is sent to an ammonia storage tank. Bottom stream 29 from the column 136 is organic waste, mostly composed of dimethyl ether. Bottom stream 24 from the column 134 is sent to the DMC separation unit shown in FIG. 2. Stream 24 is comprised of DMC and methanol. Bottom stream 13 from the column 151 is sent to the flash column 132. Stream 13 is comprised of methanol, MC, N-MMC, TG and a small amount of catalyst. Bottom stream 15 from the flash column 132 is comprised of N-MMC, MC (minor amount), TG and a small amount of organotin catalyst. Stream 15 is combined with a small liquid slipstream 11 from the primary reactor 112 to the stream 16. The combined stream 16 is introduced to the clean-up reactor 113 (Optionally the small slipstream 11 from the primary reactor 112 may be introduced to the lower section of either the column 151 or 132). Bottom stream 18 from the clean-up reactor 113 is chilled to precipitate the heterocyclic compounds such as isocyanuric acid, 1,3,5-trimethyl triazine-2, 4,6-trione, etc. in the stream and the precipitate is removed from the filtration system 133 as solid through line 19. Liquid filtrate stream 20 from the filtration system 133 splits to two streams 21 and 22 to recycle back to primary reactor 112 and clean-up reactor 113.

The primary reactor can be a single stirred tank reactor or a multiple stirred tank reactor system depending on the production capacity of dialkyl carbonate. For example, if the primary reactor is comprised of a series of three stirred tank reactors, the cleaned alkyl carbamate/urea feed stream 7 from the prereactor 111 is suitably divided into three streams and each stream is introduced directly to three reactors. A liquid reaction stream is withdrawn from each reactor and introduced to the next reactor. The liquid reaction stream from the third reactor is sent to the first reactor. A small slipstream from the liquid reaction stream from the third reactor is combined with the bottom stream 15 from column 132 to stream 16, which is sent to clean-up reactor 113. The alcohol recycle stream such as methanol recycle stream 33 from the DMC separation unit is introduced to the first reactor as super heated alcohol vapor. The overhead vapor stream from the first stirred tank reactor is introduced to the second reactor. The overhead vapor stream from the second reactor is introduced to the third reactor. The content of dialkyl carbonate in the overhead stream from each reactor increases as the vapor stream moves from the first reactor to third reactor, resulting in the highest concentration of DMC in the overhead stream from the third reactor. Overhead stream 9 from the third reactor is combined with the overhead stream 17 from clean-up reactor 113 to stream 10, which is introduced to the distillation column 151.

Bottom stream 24 from distillation column 134 is sent to the DMC separation unit (see FIG. 2). This stream contains about 28 wt. % DMC. Stream 24 from column 134 is introduced into the extractive distillation column 137 through line 34. Overhead stream 35, which is comprised of about 98 wt. % methanol and about 2 wt. % DMC, is recycled through line 30 in FIG. 1. Bottom stream 36 is introduced into extractive solvent recovery column 138. The extractive solvent, anisole, is recovered as bottom stream 38 from column 138 and recycled back to column 137 through line 38. Overhead stream 37 from column 138 is the product DMC, which is sent to a DMC storage tank.

Diethyl carbonate (DEC) can be produced in a similar manner described above for the production of DMC. Since the mixture of ethanol and DEC does not form an azeotrope, the separation of DEC from ethanol can be carried out with a single distillation column.

Figure 3:
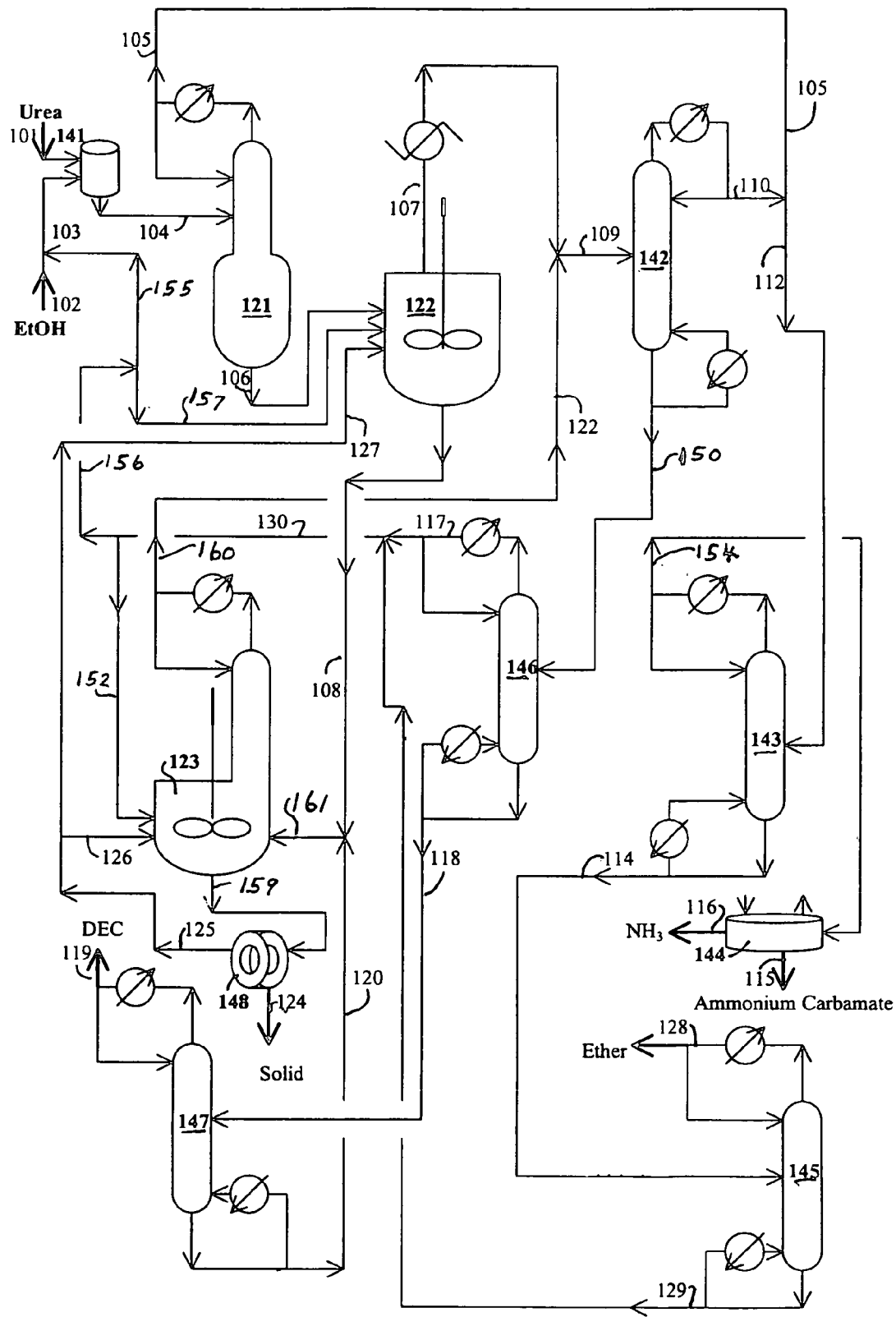
FIG. 3 is a schematic representation of a one embodiment of producing DEC according to the present invention.

FIG. 3 illustrates the simplified flow diagram of the process for the production of DEC. The urea solution is prepared in drum 141 by mixing urea feed 101 and ethanol stream 103. Ethanol stream 103 is comprised of fresh ethanol feed 102 and ethanol recycle stream 155, which is a portion of ethanol recycle stream 130. Ethanol recycle stream 130 is comprised of overhead stream 117 from distillation column 146 and bottom stream 129 from distillation column 145 (ethanol recovery column). Ethanol recycle stream 130 splits into two streams 152 and 156. Stream 152 is recycled to clean-up reactor 123. Stream 156 splits again to two streams 155 and 157 to recycle to drum 141 and primary reactor 122, respectively. Ethanol recycle stream 157 is introduced to primary reactor 122. The urea solution 104 from drum 141 is introduced to the middle of upper narrower column section of the double diameter tower reactor 121. Reactor 121 serves as a prereactor to clean up the impurities (water and ammonium carbamate) in the feeds, ethanol and urea, and to partially convert urea to EC. Vapor stream 105 from prereactor 121 is composed of ammonia, carbon dioxide and ethanol. The cleaned mixed solution is removed from prereactor 121 as bottom stream 106. Stream 106 is introduced to primary reactor (stirred tank reactor or optionally bubble column reactor) 122. Recycle ethanol stream 157 (this stream is the major portion of the ethanol recycle stream 130) is introduced into the primary reactor 122 as superheated ethanol vapor. A small slipstream 108 from primary reactor 122 is combined with bottom stream 120 from DEC recovery column 147 to form stream 161 and combined stream 161 is introduced to clean-up reactor 123. Slipstream 108 is composed of ethanol, ammonia, diethyl ether, DEC, ethyl carbamate, N-ethyl ethyl carbamate, TG, heterocyclic compounds such as isocyanuric acid, 1,3,5-triethyl triazine-2,4,6-trione, etc and organotin complex catalyst. Stream 120 is comprised of ethanol, ethyl carbamate, N-ethyl carbamate, TG, and trace amounts of catalyst. Overhead stream 160 from clean-up reactor 123 is comprised of ammonia, $CO_2$, diethyl ether, ethanol, and DEC. Bottom stream 159 from the clean-up reactor 123 is comprised of ethyl carbamate, triglyme, N-ethyl ethyl carbamate, ethanol, heterocyclic compounds and homogeneous organotin catalyst. Bottom stream 159 from reactor 123 is cooled to precipitate heterocyclic compounds in the cooling/filter system 148. The precipitate solid by-product is removed from system 148 through line 124. Liquid stream 125 from system 148 splits into two streams 126 and 127 to recycle to primary reactor 122 and clean-up reactor 123. Overhead stream 107 from primary reactor 122 is combined with overhead stream 160 from clean-up reactor 123 to stream 109. Overhead vapor stream 107 from primary reactor 122 is composed of ammonia, $CO_2$, diethyl ether, ethanol, ethyl carbamate, N-ethyl ethyl carbamate, DEC, TG and trace amount of catalyst. Stream 107 is combined with overhead stream 160 from clean-up reactor 123 to stream 109. Overhead stream 160 is comprised of ammonia, $CO_2$, diethyl ether, ethanol and DEC. Combined stream 109 is introduced to distillation column 142. Overhead stream 110 from column 142, which is composed of ammonia, $CO_2$, diethyl ether and ethanol, is introduced to distillation column 143. Overhead stream 154 from column 143 is cooled to cause the reaction of $CO_2$ with ammonia to produce ammonium carbamate. Ammonium carbamate is precipitate in liquid ammonia and removed as solids through line 115 from cooling/filter system 144. Liquid ammonia stream 116 from cooling/filter system 144 is sent to an ammonia storage tank. Bottom stream 150 from column 142 is composed of DEC, ethanol, ethyl carbamate, N-ethyl ethyl carbamate, TG and a trace amount of catalyst. Stream 150 is introduced to distillation column 146 (the first ethanol recovery column). Overhead ethanol stream 117 from column 146 is combined with ethanol bottom stream 129 from distillation column 145 (the second ethanol recovery column) to ethanol recycle stream 130. Bottom stream 118 from column 146 is introduced to distillation column 147 (DEC recovery column). Overhead stream 119 is the product DEC, which is sent to a DEC storage tank. Bottom stream 120 from column 147 is combined with a small slipstream 108 from primary reactor 122 and combined stream 161 is introduced to stirred tank clean-up reactor 123. Overhead stream 160, which is composed of ammonia, $CO_2$, diethyl ether, ethanol and DEC, is sent to column 142 through line 109. Bottom stream 114 from column 143 is sent to distillation column 145 to separate diethyl ether from ethanol in the stream. The overhead ether by-product stream 128 is sent to an ether storage tank. Bottom stream 129 from column 145 is ethanol, which is recycled to clean-up reactor 123 and primary reactor 122 through line 130.

A mixed dialkyl carbonate such as methyl ethyl carbonate (MEC) is produced by using suitable mixtures of methanol and ethanol as feed streams in place of the methanol or ethanol feed stream to the drum for the preparation of urea solution. However, the overhead streams from the primary and clean-up reactors contain some DMC and DEC in addition to MEC. DEC and DMC are separated from the mixture and the exchange reaction of DEC and DMC to MEC is carried out in a separate reactor (not shown). This exchange reaction is carried out by using either a heterogeneous base catalyst such as an alkaline form of zeolites, basic talcite, etc or a homogeneous catalyst such as Group IVB compounds such as titanium tetraethoxide or ethoxycarbonates or dialkyltin compounds such as alkoxide, dialkyltin methoxy alkyl carbonate, dialkyltin carbonate, or the organotin complex catalyst system discussed above in the absence or presence of a solvent. The suitable solvent will have a boiling point higher than about 265° F. The examples of such a solvent are hydrocarbons such as decaline, decane, xylene, diglyme, triglyme, etc or mixtures of these.

Figure 4:
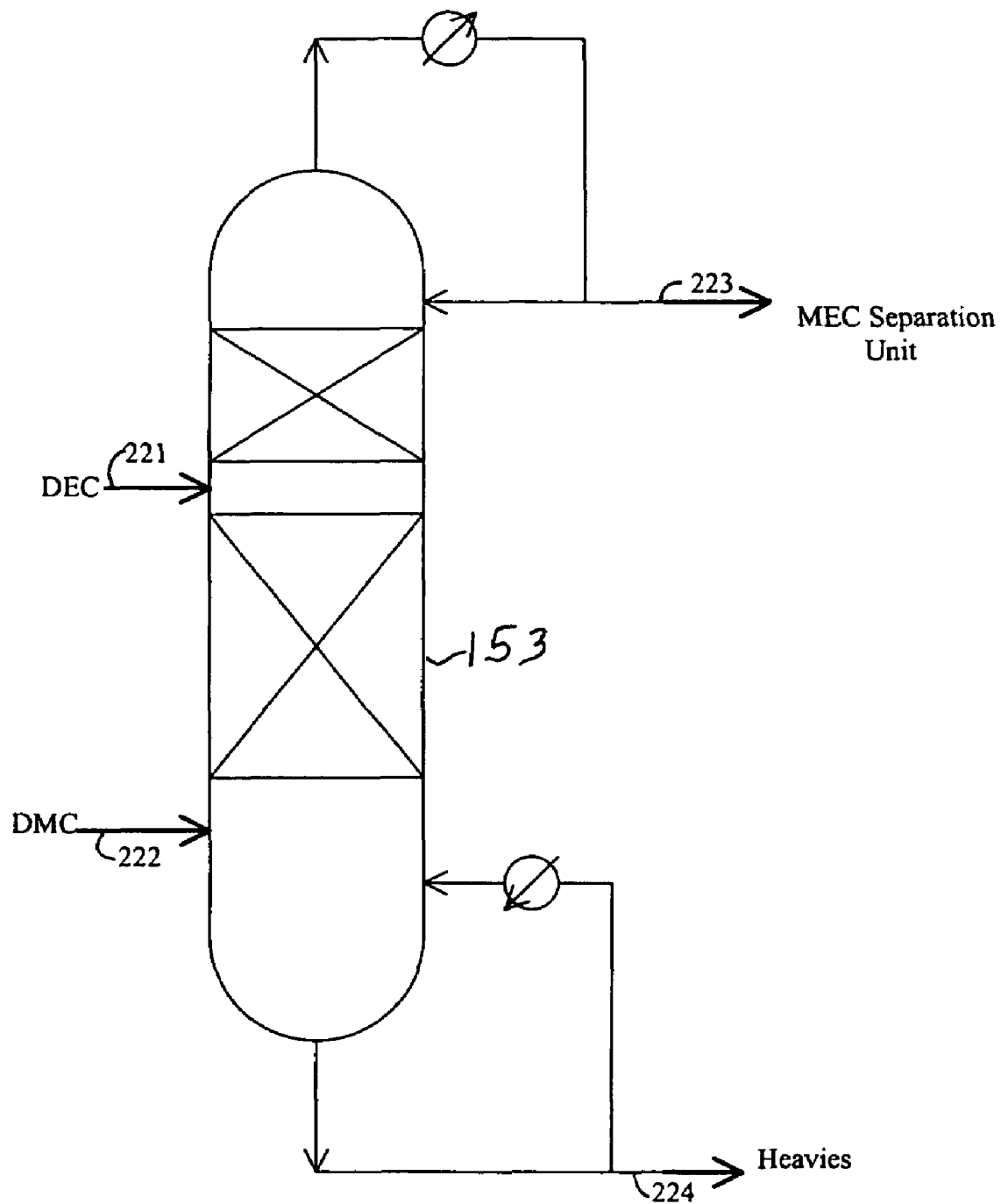
FIG. 4 is a simplified flow diagram of a reaction/distillation column reactor embodiment for the present process.

FIG. 4 illustrates a reaction/distillation column reactor using a basic heterogeneous catalyst. The DEC feed is introduced to the reaction/distillation column reactor 153 through lines 221 at a position of the top section of catalyst bed. The DMC feed is introduced to 153 at a position below the catalyst bed through line 222. The overhead stream 223 is comprised of mostly DMC and MEC. The stream 223 is sent to MEC separation unit. The temperature of the liquid catalytic reaction zone is maintained in a range from about 200 to about 450° F., preferably from 235 to 380° F. To prevent the build-up of heavies in the reboiler of column reactor 153, a small amount of bottom is withdrawn through line 224.

Figure 5:
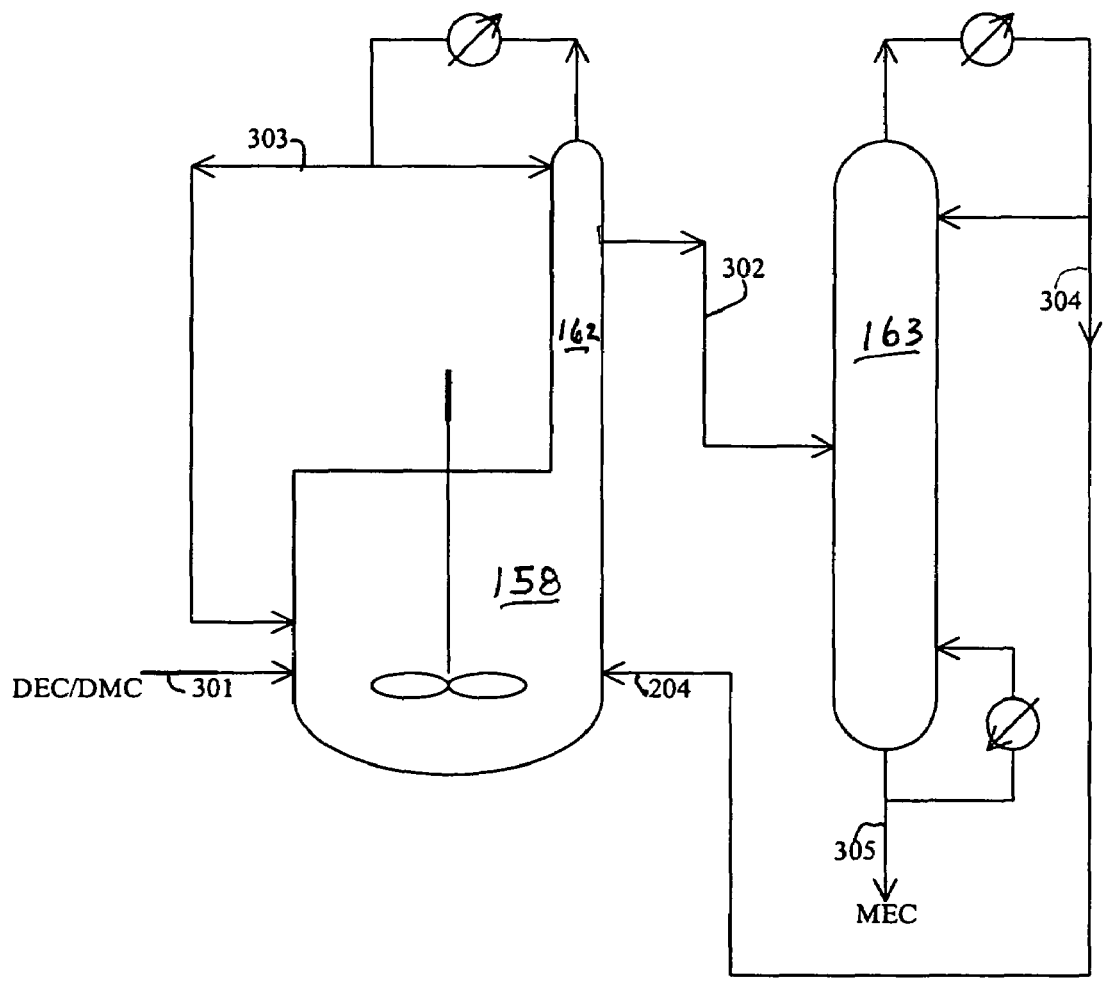

FIG. 5 illustrates a catalytic stirred tank reactor 158 with an attached distillation column 162. A homogeneous catalyst such as dibutyltin dimethoxide is used. A predetermined amount of a homogeneous catalyst is charged into reactor 158 prior to carrying out the reaction. A mixed DEC/DMC feed is introduced to reactor 158 through line 301. The overhead stream 303 from 162 is comprised of mostly DMC and a small amount of MEC is recycled back to reactor 158. A side draw stream 302, which is concentrated with MEC, from distillation column 162 is sent to distillation column 163 to separate MEC from DMC. The overhead stream 304 from column 163 is recycled back to reactor 158. The bottom MEC stream 305 from column 163 is sent to a MEC storage tank. The temperature of the liquid catalytic reaction zone is maintained in a range from about 200 to about 450° F., preferably from 235 to 380° F. The range of the overhead pressure of column 162 is from about 20 psig to about 150 psig, preferably from about 25 to about 120 psig. But the overhead pressure of column 162 is determined by the intended temperature of liquid reaction medium in 158, the composition of the reaction medium, and whether a solvent is used or not.

EXAMPLE 1

The reaction of water with urea is carried out in this example. The following materials are charged in a 500 ml three neck flask equipped with a magnetic stirrer and water cooled reflux condenser: 229.67 grams triethylene glycol dimethyl ether (triglyme), 1.58 grams of water, 2.06 grams of methanol and 15.89 grams of urea. When the reaction temperature of the mixture in the flask reaches about 100° C., 3.2 grams of additional methanol are added. The reaction of water with urea is carried out at a temperature from 128 to 140° C. for 0.92 hours under nitrogen blanket. The analysis of the sample taken from the flask are carried out by GC and HPLC. The analytical results indicate 22.4% conversion of urea and 45.2% conversion of water.

EXAMPLE 2

General Description of the Experiment

A one liter stirred autoclave serves as the reaction zone and reboiler for the reaction/distillation column reactor, which is connected to a 1 inch diameter×3.5 feet long distillation column. The distillation column has three zone heaters, which are independently controlled. The overhead vapor stream from the distillation column is diluted with a nitrogen stream (800 cc/min) and then partially cooled to about 200° F. with hot water in a condenser. The vapor stream from the condenser cooled to ambient temperature to prevent the plugging problem of a cold spot and overhead backpressure regulator. The liquid stream from the condenser flows to a small overhead liquid reflux drum. The temperature of the liquid reflux drum is maintained at ambient temperature. The flow of the liquid product from the overhead reflux drum is monitored with a LFM (liquid flow meter). The liquid stream from the overhead reflux drum and the cooled vapor stream are combined as product stream from the reaction/distillation reactor. Samples are taken for analyses to determine the composition of the overhead vapor stream coming out of the column. Also occasionally samples are taken from the reboiler to monitor the composition of the liquid reaction medium. Whenever the samples are taken from the reboiler, the make-up solutions are pumped in to compensate for the loss of triglyme and catalyst. During the operation of the reactor, the liquid level inside the reboiler is maintained at a constant level. A vertical sight glass is attached to the reboiler for the visual observation of the liquid level inside the reboiler during the operation. Also the reboiler is equipped with a liquid level digital monitor for the automatic control of the reactor during the night and weekends for unattended operation.

To carry out the operation of the primary reactor to produce DMC, a MC feed solution (methyl carbamate in methanol) and a methanol feed are pumped in and combined into a single stream. The combined feed stream is passed through a prereactor (a vertically mounted tubular reactor up-flow) at 300° F. and 230 psig to remove water in the feed streams and then introduced to the primary reactor. The temperature of the liquid reaction medium is controlled by adjusting the overhead pressure of the distillation column and the concentration of high boiling solvent in the reboiler of the distillation column. The products DMC, ammonia and other light by-products such as dimethyl ether and $CO_2$ are boiled off from the liquid medium and carried away along with methanol vapor. The operation of the distillation column is carried out in the unconventional mode to perform partial condensation of the vapor coming out of the liquid medium in the reboiler without liquid reflux from the overhead reflux drum by controlling the vapor temperature, which is done by controlling the zone temperatures of the column with three column zone heaters, while the vapor is coming up the distillation column. It was discovered that the unconventional column operation keeps the triglyme solvent in the reactor and continuously removes the by-product N-MMC along with MC from the liquid reaction medium as a part of the overhead stream, which allows the operation of the reactor for an extended period of time. It is found that no liquid reflux from the overhead reflux drum is highly preferred in minimizing the formation of the by-product N-MMC and heterocyclic compounds. It was possible to operate the reaction/distillation column reactor more than 1000 hours without interruption until a high pressure nitrogen valve to the reboiler was accidentally opened. Operating the distillation column in the conventional way causes shutdown or removal of materials from the reboiler, because of the overflow of the reboiler due to the accumulation of the reaction by-products such as N-MMC, cyanuric acid and TTT (1,3,5-trimethyl triazine-2,4,6-trione), etc.

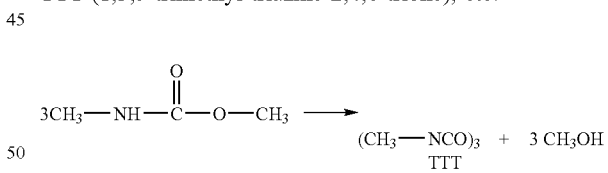

Other critical factors to minimize the side-reactions while maintaining an acceptable DMC production rate are balancing the concentrations of solvent and catalyst, the temperature of liquid medium and the overhead column pressure. The range of optimum operation for the reboiler temperature and the overhead column pressure is from about 330 to about 355° F. for the reboiler temperature and from about 80 to about 110 psig respectively.

Detailed Description of the Experiment

The reboiler of the distillation column was loaded with the following materials; 285 grams of triglyme, 100 grams of methanol and 100 grams of dibutyltin dimethoxide. A steady state operation of the reaction/distillation column reactor was obtained, while pumping in the 13.3 wt. % MC solution in methanol (~280 ppm $H_2O$) at a fixed rate of 3.01 ml/min and about 1.92 ml/min of methanol (~80 ppm $H_2O$) at 345° F. for the liquid reaction medium in the reboiler, 260° F. for the vapor temperature in the top section of the distillation column, and 90.8 psig for the overhead column pressure. The flow rate of methanol was adjusted to maintain a constant temperature of 345° F. for the liquid reaction medium. The stirring rate of the reboiler was 300 rpm. Under this operational condition, the overhead product stream was composed of ammonia, dimethyl ether, carbon dioxide, DMC, MC, NMMC, water, unknowns and a trace amount (~1000 ppb) of catalyst. At 926 hours on stream time, the overheads and the bottoms samples were taken. The analyses of these samples are listed in Table 1. The mole ratio of $MC/CH_3OH$ and DMC wt. % based on MC and $CH_3OH$ in the liquid medium in the reactor are 1.01 and 4.49 wt. % respectively, which interestingly compare with 2–10 and 1–3 wt. % claimed in U.S. Pat. No. 5,561,094 (1996, EXXON Chem). The result of the experiment corresponds to better than 95 mole % of MC to DMC. This experimental data is used to carry out computer simulation for the process design.

TABLE 1

| Sample Analysis (wt. %) | OVHD | BTM |
| --- | --- | --- |
| $CO_2$ | 0.10 | 0.04 |
| $NH_3$ | 0.73 | 0.00 |
| $(CH_3)_2O$ | 0.04 | 0.00 |
| Methanol | 90.45 | 11.02 |
| DMC | 8.15 | 1.67 |
| MC | 0.36 | 26.17 |
| N-MMC | 0.17 | 1.88 |
| TG | 0.00 | 40.89 |
| Unknown | 0.01 | 0.31 |
| TTT | 0.00 | 3.66 |
| Water (ppm) | 87 | — |
| Sn (ppm) | ~1 | 14.35* |

*as dibutyltin dimethoxide

EXAMPLE 3

A one liter stirred reactor (autoclave) with a distillation column was used to remove impurities in an 8.03 wt. % urea solution in methanol and convert urea to methyl carbamate. No catalyst was charged to the reactor. The experiment was carried out at 315° F. under 200 psig and 328° F. under 230 psig by pumping in the urea solution into the reactor at 4 ml/min with the constant bottom flow rate at 2 ml/min for 27 hours and 3 ml/min with the constant bottom flow rate at 1.5 ml/min to the end (146 hours on stream time) of the run. The distillation column is operated with overhead reflux. During the operation, the overhead flow was adjusted to maintain a constant liquid level (50% full) in the autoclave. The column operation was done with overhead reflux from the overhead reflux drum. The MC concentration in the bottom stream from the autoclave was about 20% on average, which corresponds to about 97% conversion of urea to MC. The urea feed contained about 2000 ppm water. The bottom products contained 375 ppm water at 315° F. and 300 ppm water at 328° F. on average.

EXAMPLE 4

The purpose of this experiment is demonstrating a primary reactor system, which is composed of multiple reactors. The same experimental set-up in Example 2 was used to demonstrate the performance of the second primary reactor. The experiment was carried out in the similar manner to the Experiment 2. The present example differs from the Example 2 in that the 8 wt. % DMC solution in methanol is used herein in the place of pure methanol in the Experiment 2 and a slightly lower overhead pressure (88 psig) in the present distillation column. The reboiler of the distillation column was loaded with the following materials; 285 grams of triglyme, 40 grams of methanol and 100 grams of dibutyltin dimethoxide. A steady state operation of the distillation column reactor was obtained, while pumping in MC solution and DMC-methanol solution to the reactor. The reactor operation was continued for more than 1500 hours without interruption at 345° F. for the liquid reaction medium in the reboiler, the distillation column temperature of ~278° F., and 88 psig for the overhead column pressure. The average compositions of the overhead and bottom products from the reactor during the 54 hours from 1428 hours to 1482 hours of on-stream-time are listed in Table 2. During this period, the pumping rate of a 22.5 wt. % MC solution (~590 ppm $H_2O$) was fixed at 1.97 ml/min and the pumping rate of a 8 wt. % DMC solution (80 ppm $H_2O$) was about 3.2 ml/min at 345° F. The mole ratio of $MC/CH_3OH$ and DMC wt. % based on MC and $CH_3OH$ in the liquid medium in the reactor are 0.915 and 6.40 wt. % respectively. The result of the experiment corresponds to better than 93 mole % of MC to DMC.

TABLE 2

| Sample Analysis (wt. %) | OVHD | BTM |
| --- | --- | --- |
| $CO_2$ | tr | — |
| $NH_3$ | 0.89 | — |
| $(CH_3)_2O$ | 0.06 | — |
| Methanol | 84.91 | 13.32 |
| DMC | 12.35 | 2.68 |
| MC | 1.41 | 28.58 |
| N-MMC | 0.36 | 2.28 |
| TG | 0 | 36.55 |
| HC* | 0 | 3.77 |
| Catalyst** | | 12.83 |
| Water (ppm) | 39 | — |
| Sn (ppm) | 0.6 | — |

*HC; isocyanic acid and 1,3,5-trimethyl triazine-2,4,6-trione
**as dibutyltin dimethoxide

EXAMPLE 5

The purpose of this experiment is demonstrating the production of diethyl carbonate (DEC). DEC was produced by reacting ethyl carbamate (EC) with ethanol. The experiment was carried out in the similar manner to the Example 2. An ethyl carbamate solution in ethanol and ethanol were used in place of MC solution and methanol respectively in Example 2. The reboiler of the distillation column was loaded with the following materials; 180 grams of triglyme, 100 grams of ethanol and 100 grams of dibutyltin dimethoxide. A steady state operation of the distillation column reactor was obtained, while pumping in an ethyl carbamate (EC) solution at a constant flow rate and adjusting the ethanol pumping rate to maintain a constant temperature of the liquid reaction medium. The reactor operation was continued for 340 hours without interruption at ~345° F. of the liquid reaction medium in the reboiler, the distillation column temperature of ~282° F., and a constant overhead pressure of 66 psig with an autoclave stirring rate of 300 rpm. The pumping rate of a 15.35 wt. % EC solution (~275 ppm H₂O) was fixed at 2.69 ml/min and the average pumping rate of ethanol (~106 ppm H₂O) was 2.36 ml/min. The overhead vapor stream at the top of the column was mixed with nitrogen dilution gas (600 cc/min) and then cooled to about 200° F. in a water cooled condenser. The average compositions of the overhead products and the composition of the bottom products for the entire run are listed in Table 3. 74.2 grams of solid material were removed from the reactor at the end run, which was a mixture of heterocyclic compounds and contained 670 ppm Sn by weight. The analysis of the bottom product in Table 3 indicates that the mole ratio of $EC/C_2H_5OH$ and DEC wt. % based on EC and ethanol in the liquid medium in the reactor was 0.939 and 11.08 wt. % respectively. The mass balance and urea mole balance for the entire run were 102% and 101%, respectively. The run result indicates 57.5% conversion of EC and 91 mole % selectivity of EC to DEC. The experimental result translates to DEC space yield of 1.60 $lb/h/ft^3$.

TABLE 3

| Sample Analysis (wt. %) | OVHD | BTM |
|---|---|---|
| $CO_2$ | tr | — |
| $NH_3$ | 0.50 | — |
| Ether | 0.02 | 0.11 |
| Ethanol | 90.21 | 17.60 |
| DEC | 7.30 | 5.50 |
| EC | 1.74 | 32.00 |
| N-EEC | 0.15 | 1.75 |
| TG | 0.04 | 21.05 |
| Unknown | 0.04 | 9.34 |
| HC* | 0.00 | 0.95 |
| Catalyst** | — | 11.70 |
| Water (ppm) | 148 | — |
| Sn (ppm) | 1.7 | — |

*HC; isoycanic acid and 1,3,5-triethyl triazine-2,4,6-trione
**as dibutyltin dimethoxide

The invention claimed is:

1. A process for the production of dimethyl carbonate comprising the steps of:
    (a) feeding a stream containing urea, methanol, water and ammonium carbamate to a first reaction/distillation zone:
    (b) concurrently in said first reaction/distillation zone,
        (i) reacting water with urea to form ammonium carbamate,
        (ii) decomposing the ammonium carbamate in the feed and the ammonium carbamate from the reaction of water with urea into ammonia and carbon dioxide, and
        (iii) separating the ammonia, carbon dioxide and methanol from the urea and by distillation;
    (c) removing ammonia, carbon dioxide and methanol from said first reaction/distillation zone as a first overheads;
    (d) removing urea and methanol from said first reaction/distillation zone as a first bottoms;
    (e) feeding said first bottoms and methanol to a second reaction/distillation zone;
    (f) concurrently in said second reaction/distillation zone,
        (i) reacting methanol and urea in the presence of a homogeneous catalyst comprising an organotin complex compound of dialkylmethoxide in a high boiling solvent to form dimethyl carbonate and
        (ii) separating dimethyl carbonate and ammonia from the homogeneous catalyst by distillation;
    (g) removing dimethyl carbonate and methanol from said second reaction/distillation zone as a second overheads; and
    (h) removing a second bottoms from said second reaction/distillation zone.

2. The process according to claim 1 wherein the dimethyl carbonate in said second overheads is separated from the methanol by extractive distillation.

3. The process according to claim 1 wherein an inert diluent is added to said first overheads.

4. The process according to claim 1 wherein the methanol in said first overheads is condensed and a portion of said condensed methanol is returned to near the top of said first reaction/distillation zone as reflux and the remainder of said condensed methanol is returned to the lower section of said first reaction/distillation zone.

5. The process according to claim 1 wherein a first portion of said second bottoms is fed to said reaction/distillation zone, a second portion of said second bottoms is recycled to said second reaction/distillation zone and a third portion of said second bottoms is fed to a third distillation column reactor for catalyst regeneration and heavies cleanup.

6. The process according to claim 1 wherein said second overheads is condensed and a portion of said condensed second overheads is returned to said second reaction/distillation zone as reflux.

* * * * *

UNITED STATES PATENT AND TRADEMARK OFFICE
CERTIFICATE OF CORRECTION

PATENT NO.       : 7,074,951 B2                                Page 1 of 1
APPLICATION NO.  : 10/821225
DATED            : July 11, 2006
INVENTOR(S)      : Ryu et al.

It is certified that error appears in the above-identified patent and that said Letters Patent is hereby corrected as shown below:

Column 3, in the formula, line 21,

"$(CH_3)_2CO + CH_3NH_2$" should be --$(CH_3\text{-}0)_2C=0 + CH_3NH_2$--.

Column 8, in the formula, line 20,

"$R\text{-}O\text{-}\overset{\overset{OH}{\|}}{C}\text{-}N\text{-}R + R\text{-}OH + CO_2$"

should be

--$R\text{-}O\text{-}\overset{\overset{O}{\|}}{C}\text{-}NH\text{-}R + R\text{-}OH + CO_2$--.

Column 9, in the formula, line 10 and 11,

"$R\text{-}O\text{-}\overset{\overset{O}{\|}}{C}\text{-}NH_2 + NH_3 + ROH \Longleftrightarrow (RO)_2CO + 2NH_3$"

should be

--$R\text{-}O\text{-}\overset{\overset{O}{\|}}{C}\text{-}NH_2 + ROH \Longleftrightarrow (R\text{-}O)_2C=O + NH_3$--.

Column 11, line 4, after the word "dialkyl" the word --carbonate-- is erroneously missing.

Signed and Sealed this

Eighteenth Day of September, 2007

JON W. DUDAS
*Director of the United States Patent and Trademark Office*